United States Patent [19]

Robicsek

[11] Patent Number: 5,447,515

[45] Date of Patent: Sep. 5, 1995

[54] CORONARY BYPASS CLAMP

[75] Inventor: Francis Robicsek, Charlotte, N.C.

[73] Assignee: Pilling Co., Fort Washington, Pa.

[21] Appl. No.: 193,445

[22] Filed: Feb. 8, 1994

[51] Int. Cl.⁶ .......................................... A61B 17/122
[52] U.S. Cl. .................................... 606/158; 606/207
[58] Field of Search .................. 606/1, 151, 157, 158, 606/205–209, 210, 211; 294/99.1, 99.2, 118; 30/178

[56] References Cited

U.S. PATENT DOCUMENTS

| 3,277,895 | 10/1966 | Johnson . | |
| 3,996,937 | 12/1976 | Williams . | |
| 4,024,868 | 5/1977 | Williams . | |
| 4,817,287 | 4/1989 | Arnold et al. | 30/178 |
| 4,873,975 | 10/1989 | Walsh et al. . | |

OTHER PUBLICATIONS

Surgical Instruments Catalog–The Lawton Co., Inc. 1957 pp. 287, 288, 450.
Pilling Surgical Instruments Catalog, Pilling Co., 1993.

Primary Examiner—Stephen C. Pellegrino
Assistant Examiner—Glenn Dawson
Attorney, Agent, or Firm—Howson & Howson

[57] ABSTRACT

A ring-handled bypass clamp provide a spoon-shaped blade insertable through a temporary incision in the ascending aorta and a cooperating ring positionable on the exterior of the aorta opposite to the blade. An aortotomy is performed on the portion of the aorta wall inside the ring to provide an annular portion of the wall to which a graft is sutured.

24 Claims, 2 Drawing Sheets

CORONARY BYPASS CLAMP

BRIEF SUMMARY OF THE INVENTION

This invention relates generally to surgical instruments, and more particularly to a surgical clamp and a surgical procedure in which the clamp is used in carrying out an aortocoronary bypass.

Bypass operations provide an alternate conduit for blood to flow, around occluded segments of arteries or veins. The most common of these is a lateral anastomosis for the treatment of coronary artery diseases caused by atherosclerosis or narrowing of the small arteries between the aorta and the heart muscles. A section of saphenous vein, or a suitable substitute, is grafted, usually between the ascending aorta just above the heart and one or more of the coronary arteries beyond the points of blockage. As many as six grafts may be carried out in an individual patient depending on the circumstances. The operation is performed with the patient connected to a heart-lung machine and the heart stopped. A conventional side-biting aortic clamp pinches a folded side of the ascending aorta wall near the heart to form an occluded site for an aortotomy in order to prevent loss of blood.

The side-biting aortic clamp, however, has shortcomings. In some cases, for example, it adds further risks where atheromatous plaque has accumulated in a patient's ascending aorta. When the heart-lung machine and clamp are removed and natural circulation is restored, this plaque may dislodge and be carried through the carotid arteries to the brain, where it can cause serious cerebral damage. Furthermore, cutting only one folded section of the pinched wall and suturing a graft to it for a lateral anastomosis can be difficult and time consuming. This is due, in part, to the fact that the aorta is only about 25 mm in diameter, and the pinched wall section formed by the bite of the side-biting clamp is only a relatively small portion of the aorta. Still another problem with the conventional side-biting clamp is that, unless great care is taken in carrying out the aortotomy, there is a possibility of damaging other portions of the aorta wall. It is therefore apparent that there is a need for a surgical clamp which will reduce the risk of dislodging life-threatening atheromatous plaque, and provide a site readily accessible for aortotomy and suturing for a lateral anastomosis.

Accordingly, one object of this invention is to provide an improved bypass clamp suitable for use in grafting a lateral anastomosis to a blood vessel in a patient.

Another object is to provide a clamp which will hold an occluded portion of the ascending aorta wall in a readily accessible position for grafting a lateral anastomosis thereto in a coronary bypass operation.

Still another object is to provide a coronary bypass clamp which can be applied with reduced risk of dislodging life-threatening atheromatous plaque accumulated in the ascending aorta of a patient.

A further object is to provide a coronary bypass clamp which provides a site in the ascending aorta suitable for performing an aortotomy and for attaching a lateral anastomosis with a minimum loss of blood.

A still further object is to provide an improved method for performing a lateral anastomosis.

Briefly, these and other objects of the invention are achieved with a bypass clamp having a pair of handles pivoted together in the middle, each having a connected finger grip on one end and a ring and a bowl-shaped blade, respectively, on opposed distal ends for sealingly clamping opposite sides of the wall of a blood vessel. As applied in a lateral anastomosis of a blocked blood vessel, the blade is inserted through a temporary incision in the vessel and positioned, above a blockage, at a selected site for attaching a graft. The clamp is then closed, causing the ring to secure the wall of the vessel over the blade and form a continuous annular seal between the wall and the rim of the blade. A generally circular aortotomy is then made in the wall within the ring leaving a portion of the wall around the opening sufficient for suturing one end of a graft. The blade-wall seal prevents blood from escaping through the opening during this process. The distal ends of the clamp are then opened to draw the free end of the graft through the ring after which the blade can be withdrawn through the temporary incision. The anastomosis may now be completed by suturing the free end of the graft at a point communicating with the vessel beyond the blockage, and permanently closing the temporary incision.

BRIEF DESCRIPTION OF THE DRAWINGS

Other objects, novel features and advantages of the invention will become more apparent from the following detailed description when considered in conjunction with the accompanying drawings, wherein.

DETAILED DESCRIPTION

Figure 1:
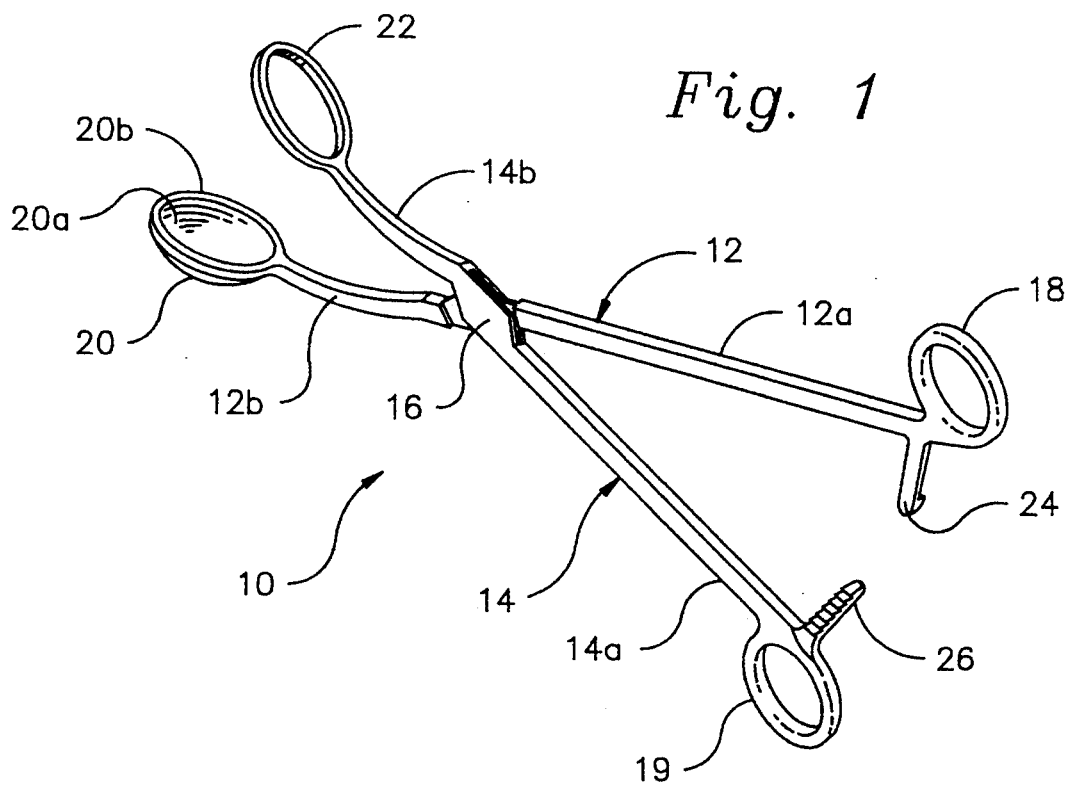
FIG. 1 is an isometric view of one embodiment of a clamp constructed according to the invention suitable for use in coronary bypass surgery.
Figure 2:
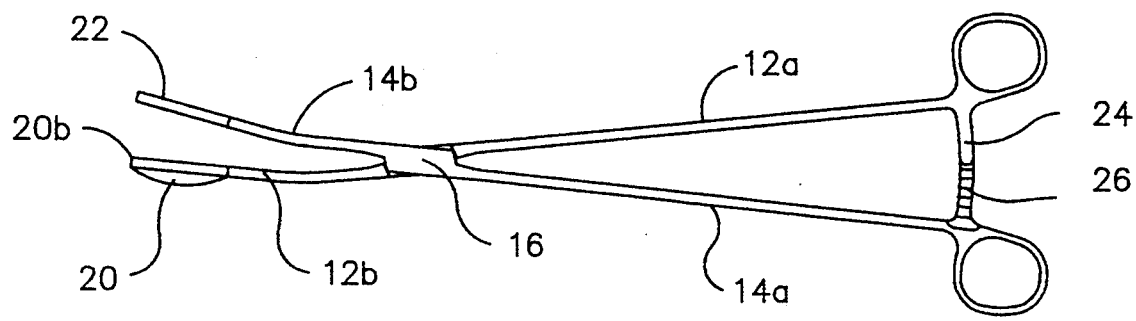
FIG. 2 is an elevational view of the clamp of FIG. 1.

Referring now to the drawings wherein like characters designate like or corresponding parts throughout the several views, FIG. 1 shows a clamp suitable for use in coronary bypass surgery comprising a pair of elongate handles 12 and 14 of steel, such as Type 410X martinsitic stainless steel, pivotally connected on an axis intermediate opposite ends thereof by a substantially stress-free hinge integrally formed in a box lock-joint 16 such as disclosed in U.S. Pat. No. 3,952,749 to John Fridolph et al. Handles 12 and 14 are defined by substantially straight arms 12a and 14a, extending from joint 16 and terminating with ring-shaped finger grips 18 and 19 for opening and closing the instrument by a scissors-like manipulation; and by curved arms 12b and 14b, extending from joint 16 in the same plane of motion as arms 12a and 14a, and terminating with a blade 20 and ring 22, respectively. As more clearly shown in FIG. 2, arms 12b and 14b gradually diverge in the same direction from the respective longitudinal axes of arms 12a and 14a near lock-joint 16.

Figures 6A, 6B, 7A, 7B:
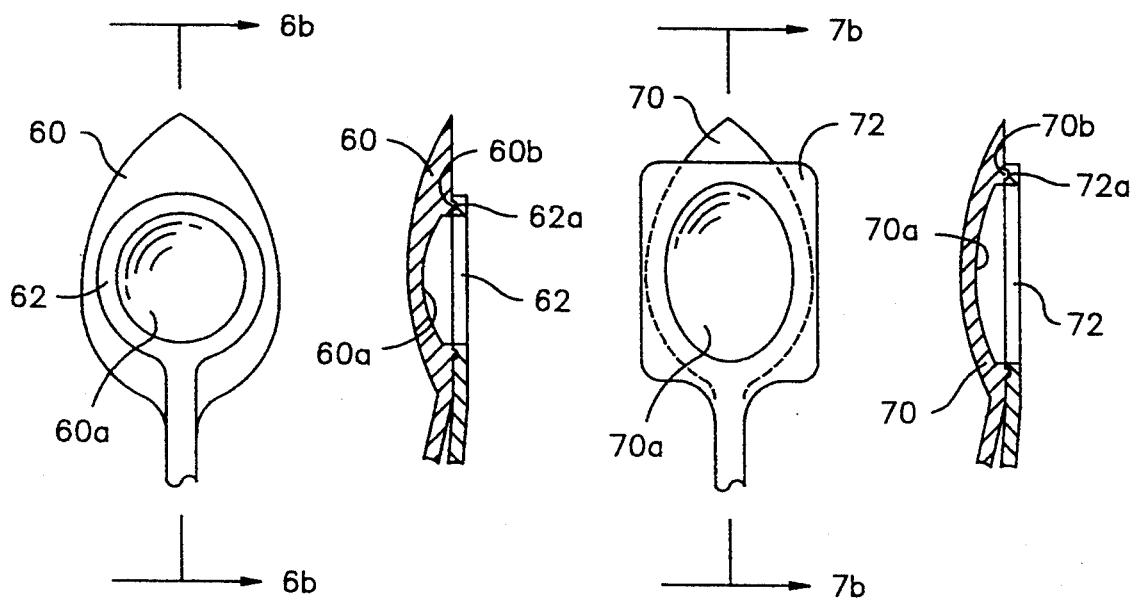
FIGS. 6a and 6b are fragmentary plan and cross-sectional views respectively of another blade and ring configuration for a clamp according to the invention.
FIGS. 7a and 7b are fragmentary plan and cross-sectional views of still another configuration of a blade and ring according to the invention.

Blade 20 defines a generally circular bowl 20a with a rim 20b situated in a plane parallel to the facing side of ring 22 when clamp 10 is closed in a normal clamping position. The circumference of rim 20b and ring 22 are congruent, thus assuring a relatively uniform clamping pressure to opposed sides of the aortic wall. Various other configurations of the distal end of the clamp 10 are contemplated depending on circumstances such as the location and size of the blood vessel, nature of the anastomosis, and surgeons' preferences. Two other examples are illustrated in the drawings. FIGS. 6a and 6b show a spoon-shaped blade 60 with a generally circular bowl 60a and a raised rim 60b. The perimeter of a rim 60b around the bowl is congruent with an annular groove 62a in the facing side of a ring 60. FIGS. 7a and 7b show another spoon-shaped blade 70 with an oval-shaped, generally elliptical, bowl 70a and a raised rim 70b around the recess which is congruent with a continuous groove 72a around the facing side of a ring 72.

As shown in FIG. 1, lugs 24 and 26, adjacent to grips 18 and 20, project laterally toward each other from arms 12a and 14a to form a ratchet for locking clamp 10 in the closed position when blade 20 and ring 22 are manually squeezed together. The stiffness of the handles and the locking position of lugs 24 and 26 determine the clamping force.

By way of illustration but not of limitation, a typical clamp as described above, suitable for aortocoronary bypass surgery is constructed with an overall length of 16 cm, including blade 20 and ring 22 which are each 15 mm long. The blade width and depth are 8 or 11 mm and 6 mm, respectively. Curved arms 12b and 14b each have a radius of curvature of 2.0 cm and cord length of 1.9 cm. The dimensions, of course, are approximate and will vary according to requirements and personal preferences of the surgeon.

Figure 3:
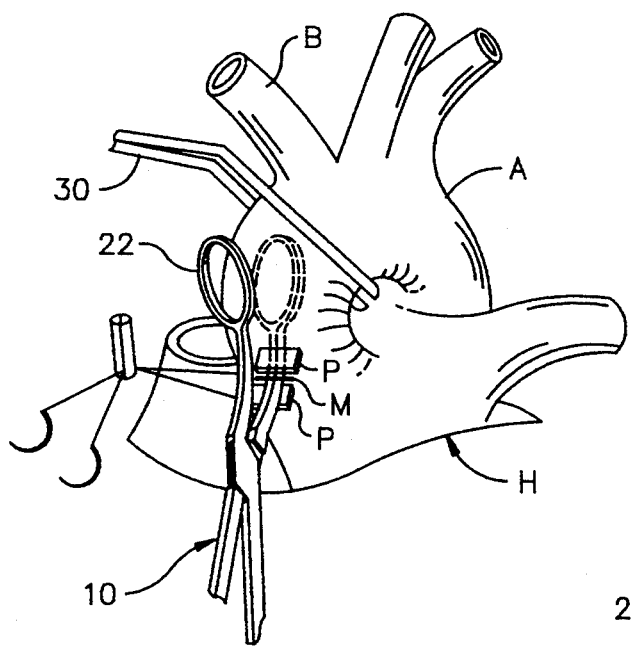
FIG. 3 is an anterior view of an ascending aorta with a blade and ring at distal ends of the clamp of FIG. 1 positioned at a site selected for an aortotomy.
Figure 4:
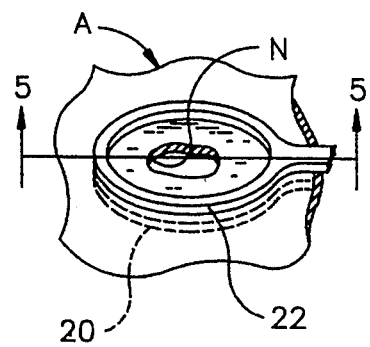
FIG. 4 is a fragmentary perspective view showing the blade and ring of FIG. 3 after being secured to the wall of the aorta around the aortotomy.
Figure 5:
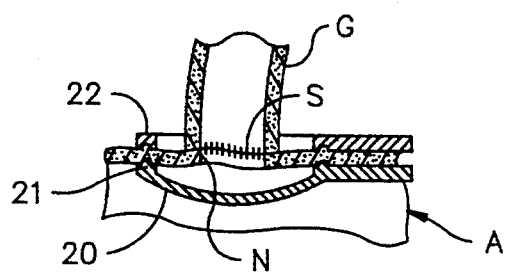
FIG. 5 is a cross-sectional view of the blade and ring taken on plane 5—5 of FIG. 4, with a graft end sutured to the aorta.

The manner in which clamp 10 is utilized in a aortocoronary bypass surgical procedure is illustrated in FIGS. 3-5. Referring first to FIG. 3, the ascending aorta A is totally occluded proximal to the innominate artery B by jaws 30 of a cross-clamp to prevent backflow of blood from a heart-lung machine (not shown) which is connected beyond the cross-clamp. A temporary incision M is made in the ascending aorta A, at a location near the heart H, for insertion of blade 20 of clamp 10 so that it can be moved toward the site selected for an aortotomy. Patches P of saphenous vein or suitable substitute may be sutured on either side of the incision as reinforcement of the aorta to prevent tearing or abrasion by clamp 10.

As shown in FIGS. 4 and 5, when the blade is brought to the site selected for the aortotomy, clamp 10 is closed and locked by lugs 24 and 26. This causes ring 22 to form a continuous seal of the aorta wall to rim 21 of blade 20. Being totally isolated from the interior of the aorta by the plate-wall seal, a circular aortotomy N, less than the diameter of ring 22, is made with little or no loss of blood in the exposed wall within ring 22. The annular portion of the wall around the opening and within the ring is left for suturing one end of a graft G thereto.

The anastomosis is completed by opening clamp 10 and pulling the free end of graft G through ring 22 so that blade 20 can be withdrawn through incision M. The free end of graft G is then attached to the coronary artery beyond the blockage, the temporary incision closed, and the heart-lung machine disconnected upon restoration of heart function.

Some of the many advantages and novel features of the invention should now be readily apparent. For example, a bypass clamp is provided which is particularly suitable for grafting a lateral anastomosis to a blood vessel in a patient. It provides a readily accessible area around an opening in a blood vessel for suturing the graft. In a coronary bypass procedure, it reduces the risk of dislodging life-threatening atheromatous plaque accumulated in the ascending aorta of a patient, and it offers a significantly improved method for performing bypass surgery with minimal loss of blood.

It will be understood, of course, that various changes in the details, steps and arrangement of parts can be made. For example, while the preferred embodiments specifically disclosed are in the form of ring-handled instruments having a pivot joint, it is possible to realize many of the advantages of the invention in a version in which the ring and blade are interconnected by another form of linkage, for example a linkage utilizing a screw to effect movement of the blade and ring toward and away from each other. Still other modifications may be made by those skilled in the art within the principal and scope of the invention as expressed in the appended claims.

I claim:

1. A clamp comprising:
    first means providing a continuous rim around a concave surface on one side of a blade, said first means being insertable through a temporary incision in a blood vessel whereby the rim can be supported against an interior side of the blood vessel at a location remote from the temporary incision;
    second means providing a ring with one side thereof formed to be brought into a clamping position against an exterior side of the blood vessel in opposition to the rim; and
    manipulable means, connected to said first means and said second means, for effecting movement of the ring toward the rim while the blade is supported at said location to form a sealed chamber between the concave surface and the interior side of the blood vessel; whereby an incision into the blood vessel can be made through the ring.

2. A clamp according to claim 1 wherein said rim and said one side of said ring are in substantially parallel planes when in the clamping position.

3. A clamp according to claim 2 further comprising locking means connected to said first means and said second means for maintaining the blood vessel is clamped between said blade and said ring.

4. A clamp according to claim 1 further comprising a raised edge extending from said rim.

5. A clamp according to claim 4 further comprising a groove in said one side of the ring, said groove being disposed opposite to said raised edge.

6. A clamp according to claim 1 wherein said blade is spoon-shaped.

7. A clamp according to claim 1 wherein said rim is oval shaped.

8. A clamp according to claim 1 further comprising:
    a continuous groove and a raised edge around opposed faces of said rim and said ring cooperating to seal the blood vessel therebetween.

9. A clamp according to claim 1 wherein:

one of said rim and said ring includes a raised edge, and the other of them a groove interengageable with said edge.

10. A clamp comprising:
   a pair of elongate handles, each having a proximal end and a distal end, said handles being pivotally connected on an axis intermediate the proximal and distal ends for manipulating the proximal ends in a generally longitudinal plane, whereby the distal ends can be moved toward each other to a clamping position, and apart from each other to an open position;
   a blade on one of said distal ends and a ring on the other of said distal ends, said blade defining a bowl with a concave surface facing said ring and having a continuous rim formed to oppose one side of said ring when the distal ends are in the clamping position; whereby an incision into a blood vessel clamped between the blade and the ring can be made through the ring.

11. A clamp according to claim 10 wherein said rim and said one side of said ring are in substantially parallel planes when in the clamping position.

12. A clamp according to claim 11 wherein: said parallel planes are normal to said longitudinal plane.

13. A clamp according to claim 12 further comprising locking means extending from said handles for maintaining said blade and said ring in the clamping position.

14. A clamp according to claim 13 wherein portions of said handles between said axis and the distal ends are curved in one direction.

15. A clamp according to claim 10 further comprising a raised edge extending from said rim.

16. A clamp according to claim 15 further comprising a groove in said one side of the ring, said groove being disposed opposite to said raised edge.

17. A clamp according to claim 10 wherein said blade is spoon-shaped.

18. A clamp adapted for use in aortocoronary bypass surgery, comprising:
   a pair of shafts each having a proximal end and a distal end, said shafts being pivotally connected to each other with a handle fixed respectively to the proximal end of each of said shafts, said shafts being pivotable in a generally longitudinal plane between closed and open positions; and
   a blade and a ring each fixed respectively to the distal end of one of said shafts for manipulation by said handles, said blade defining a bowl with a concave surface facing said ring and having a continuous rim of size and shape for opposing one side of said ring when in the closed position;
   whereby insertion of said blade into the aorta adjacent to a selected site for an aortotomy, and manipulation of said handles to their closed position, secures opposite sides of the aorta wall between the ring and the rim of the blade, and seals the aortotomy against loss of blood; whereby an incision into the aorta wall can be made through the ring.

19. A clamp suitable for bypass surgery and similar procedures comprising, in combination:
   a pair of elongate members pivotally connected together on an axis intermediate of proximal and distal ends of said members and forming first and second pairs of arms, the arms of said first pair being moveable in a generally longitudinal plane for manipulation of said second pair of arms relative to each other between a closed position and an open position, the arms of said second pair extending in one direction in a curve within said longitudinal plane;
   a blade and a ring on the respective distal ends of said members, said blade defining a bowl with a concave surface facing said ring and having a continuous rim of size and shape positioned to oppose one side of said ring when the arms are in the closed position; whereby an incision into a vessel wall clamped between the blade and the ring can be made through the ring.

20. A method for bypass surgery of a coronary blockage comprising the steps of:
   providing an occlusion in an ascending aorta proximal to innominate artery to prevent backflow of blood from a heart-lung machine connected beyond the occlusion;
   making a temporary incision in a wall of the ascending aorta at a location near the heart;
   inserting a blade, connected to a distal end of pivotable handles, along an interior side of the wall at a site selected for an aortotomy, the blade defining a bowl with a continuous rim;
   compressing a ring connected to said handles on an exterior side of the wall adjacent to the rim to form a continuous seal of the aorta wall with the rim;
   cutting a generally circular opening in the wall within the ring, the opening having a diameter less than that of the ring, to form an annular wall portion; and
   suturing one end of a graft to said annular wall portion.

21. A method according to claim 20 further comprising the steps of:
   pulling a free end of the graft through the ring after the graft is sutured;
   withdrawing the blade from the aorta through the temporary incision;
   attaching the free end of the graft to the coronary artery for establishing communication of the aorta beyond the blockage; and
   closing the temporary incision.

22. A clamp comprising:
   a ring having an uneven surface;
   a concave blade having a rim complementary to said uneven surface and in opposition thereto for resisting slipping of a material clamped therebetween; and
   a pair of members connected to said blade and said ring for manipulating said rim and said uneven surface between open and clamping positions; whereby an incision into the material can be made through the ring.

23. A clamp according to claim 22 wherein: one of said surfaces forms a projection, and the other of said surfaces forms a recess complementary to said projection.

24. A clamp according to claim 22 wherein: said surfaces form a continuous tongue-and-groove interface.

* * * * *